(12) United States Patent
Sugiyama et al.

(10) Patent No.: US 8,495,906 B2
(45) Date of Patent: Jul. 30, 2013

(54) DEGASIFIER AND LIQUID CHROMATOGRAPH EQUIPPED THEREWITH

(75) Inventors: Koji Sugiyama, Kyoto (JP); Akira Sezaki, Kyoto (JP); Takanori Kamada, Kyoto (JP); Yoshikiyo Hongo, Shiga (JP)

(73) Assignee: Arkray, Inc., Kyoto (JP)

( * ) Notice: Subject to any disclaimer, the term of this patent is extended or adjusted under 35 U.S.C. 154(b) by 682 days.

(21) Appl. No.: 12/223,856

(22) PCT Filed: Feb. 8, 2007

(86) PCT No.: PCT/JP2007/052270
§ 371 (c)(1),
(2), (4) Date: Jul. 26, 2010

(87) PCT Pub. No.: WO2007/094242
PCT Pub. Date: Aug. 23, 2007

(65) Prior Publication Data
US 2010/0288024 A1   Nov. 18, 2010

(30) Foreign Application Priority Data
Feb. 16, 2006 (JP) .................. 2006-039529

(51) Int. Cl.
*G01N 30/00* (2006.01)
(52) U.S. Cl.
USPC ..................... 73/61.56; 73/53.01
(58) Field of Classification Search
USPC .......................... 73/61.56, 53.01
See application file for complete search history.

(56) References Cited

U.S. PATENT DOCUMENTS

| 5,205,844 A | 4/1993 | Morikawa |
| 6,315,815 B1 | 11/2001 | Spadaccini et al. |
| 6,319,398 B1 | 11/2001 | Saitoh |
| 2006/0070525 A1 | 4/2006 | Johnson et al. |

FOREIGN PATENT DOCUMENTS

| CN | 101500692 | 8/2009 |
| EP | 1 078 671 A2 | 2/2001 |
| EP | 1 529 560 A2 | 5/2005 |
| EP | 1544437 A2 | 6/2005 |
| JP | 04-030004 U | 3/1992 |
| JP | 04-203479 A | 7/1992 |
| JP | 07-120447 A | 5/1995 |

(Continued)

OTHER PUBLICATIONS

Chinese Office Action with issued Jul. 29, 2011 and its English language translation for corresponding Chinese Application No. 200780013729.0.

(Continued)

*Primary Examiner* — Hezron E Williams
*Assistant Examiner* — Rodney T Frank
(74) *Attorney, Agent, or Firm* — Rader, Fishman & Grauer PLLC

(57) ABSTRACT

The present invention relates to a deaerator 2 including: a liquid flow space; reduced-pressure spaces 25A, 25B, and 25C; gas permeable films 21A, 21B, and 21C that separate these spaces; and a pump for discharging gas from within the reduced-pressure spaces 25A, 25B, and 25C to the outside, and to a liquid chromatograph equipped with the deaerator 2. The deaerator 2 further includes gas partial pressure variation suppression means 23A, 23B, 23C, 25Ab, 25Bb, 25Cb, 29A, 29B, and 29C for suppressing variations in partial pressures of a specific gas in the reduced-pressure spaces 25A, 25B, and 25C.

25 Claims, 13 Drawing Sheets

FOREIGN PATENT DOCUMENTS

| | | |
|---|---|---|
| JP | 09-253642 A | 9/1997 |
| JP | 11-057415 A | 3/1999 |
| JP | 2000-162100 A | 6/2000 |
| JP | 2000-275229 A | 10/2000 |
| JP | 2001-133445 A | 5/2001 |
| JP | 2001-141360 A | 5/2001 |

OTHER PUBLICATIONS

Communication from European Patent Office dated Nov. 3, 2011 for application No. 07708254.3-2204.
US 4,568,648, 02/1986, Reim (withdrawn)

FIG. 11
FIG. 11A
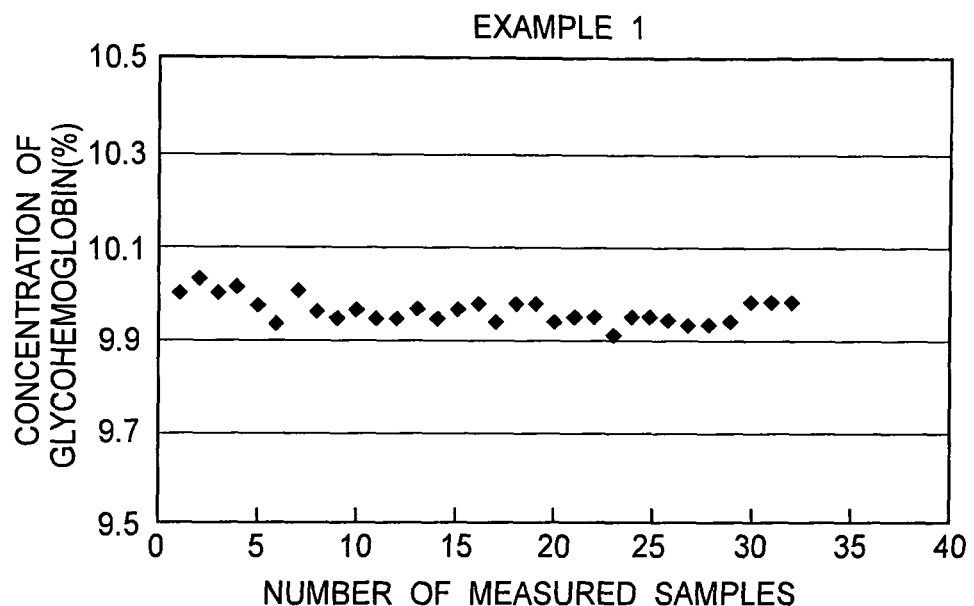
FIG. 11B
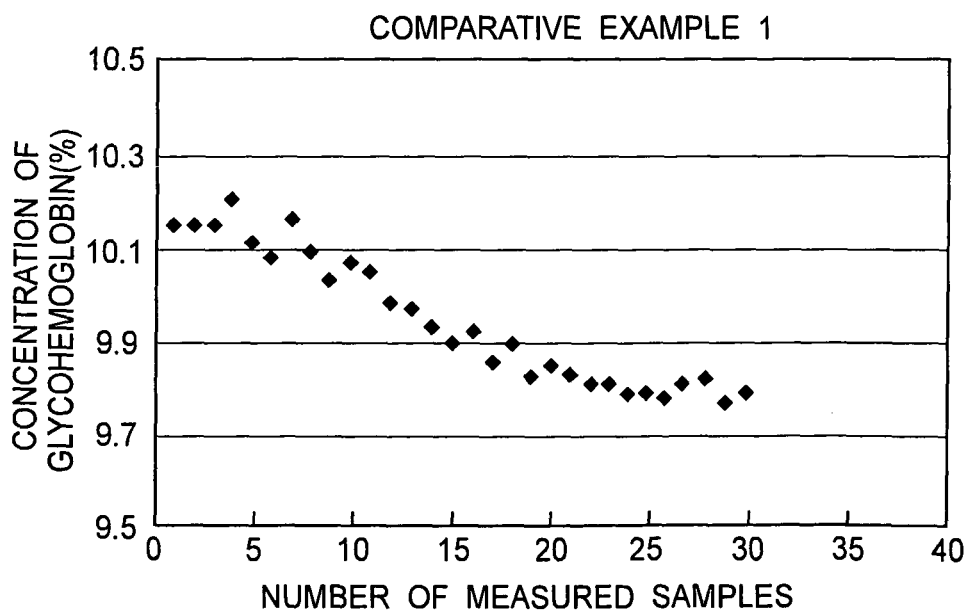

DEGASIFIER AND LIQUID CHROMATOGRAPH EQUIPPED THEREWITH

TECHNICAL FIELD

The present invention relates to a deaerator configured so as to deaerate a liquid in a liquid flow space by separating the liquid flow space from a reduced-pressure space by a gas permeable film and discharging the gas from within the reduced-pressure space to the outside by a pump, and to a liquid chromatograph equipped with the deaerator.

BACKGROUND ART

For separating and analyzing biogenic substances by using biological samples such as blood, high-performance liquid chromatographs (HPLC apparatuses) utilizing high-performance liquid chromatography (HPLC) have been widely used (for example, refer to Patent Document 1). As shown in FIG. 12, a general HPLC apparatus is configured in such a manner that, after a sample containing a biogenic substance is prepared in a sample preparation unit 90, the sample is introduced into an analysis column 91, and the biogenic substance is adsorbed on a packing material of the analysis column 91. The biogenic substance adsorbed on the packing material is eluted by supplying an eluent from an eluent bottle 93 to the analysis column 91 by using a liquid feed pump 92. The eluate from the analysis column 91 is introduced into a photometric mechanism 94, and by continuously measuring the absorbance of the eluate in the photometric mechanism 94, the analysis of the biogenic substance is carried out.

In an HPLC apparatus 9, in order to stably carry out analysis of a biogenic substance, a deaerator 95 is installed at the upstream of the liquid feed pump 92 (for example, refer to Patent Document 2). The deaerator 95 is provided so as to remove gas, such as oxygen, remaining in the eluent. The installation of the deaerator 95 into the HPLC apparatus 9 prevents formation of air bubbles from gas dissolved in the eluent, can prevent destablization of the feed rate of the liquid feed pump 92, and therefore enables the analysis of a biogenic substance in the HPLC apparatus 9 to be stably carried out.

As shown in FIG. 13, an example of a deaerator 95 is configured so as to suction and remove the dissolved gas in the eluent by passing the eluent through a gas permeable tube 97 disposed in a reduced-pressure space 96 and reducing the pressure of the reduced-pressure space 96 using a pump 98 (for example, refer to Patent Document 3). In other words, when the eluent passes through the inside of the gas permeable tube 97, the dissolved gas in the eluent is transferred to the outside of the gas permeable tube 97 (the reduced-pressure space 96), thereby being removed.

The deaerator 95 having such a configuration is also used for prevention of oxidation or prevention of development of microorganisms in manufacturing processes of food, drinking water or the like, as well as in the HPLC apparatus 9 shown in FIG. 12.

Patent Document 1 Japanese Patent Application Laid-Open No. 7-120447
Patent Document 2 Japanese Patent Application Laid-Open No. 2001-133445
Patent Document 3 Japanese Patent Application Laid-Open No. 2000-275229

DISCLOSURE OF THE INVENTION

Problems to be Solved by the Invention

However, when deaeration of an eluent is continuously performed in the deaerator 95, the partial pressure of a deaeration gas component in the reduced-pressure space 96 gradually increases due to an influence of the gas removed from the eluent. In particular, in a case in which a product made of a silicon resin, having such a property as to more easily allow oxygen permeation than nitrogen, is used as a gas permeable tube 97, the partial pressure of oxygen in the reduced-pressure space 96 easily increases. In a case in which the partial pressure of the deaeration gas in the reduced-pressure space 96 increases, the amount of the gas that can be transferred from the eluent in the gas permeable tube 97 to the reduced-pressure space 96 decreases. Therefore, in a case in which deaeration of the eluent is continuously carried out in the deaerator 95, deaeration capability lowers as the partial pressure of the deaeration gas increases, so that an expected purpose of using the deaerator 95 cannot be achieved sufficiently.

In addition, when operation of the deaerator 95 is stopped, the reduced-pressure space 96 is opened to the atmosphere so as to avoid concentration of the eluent in the gas permeable tube 97. In this case, although the partial pressure of the gas is similar to that of the atmosphere at an initial stage of driving of the deaerator 95, the partial pressure of the deaeration gas component in the reduced-pressure space 96 increases due to continuous deaeration of the eluent, as described above. Therefore, the dissolution amount of the gas component contained in the eluent (for example, the amount of dissolved oxygen) at the initial stage of driving of the deaerator 95 is different from the dissolution amount after the deaerator 95 has been driven for a fixed period of time. As a result, the measured value of the sample analyzed after driving the deaerator 95 for a certain period of time is different from the measured value of the sample analyzed at the initial stage of driving of the deaerator 95, which may lead to deteriorated measurement accuracy.

For example, in the HPLC apparatus 9 for measuring the concentration of glycohemoglobin in a blood sample, glycohemoglobin is measured in terms of the ratio of glycohemoglobin to the total amount of hemoglobin. However, it is possible that the measurement accuracy is deteriorated since hemoglobin is present in the forms of oxyhemoglobin and deoxyhemoglobin. That is, in a case in which the amount of dissolved oxygen in the eluent varies depending on the performance of the deaerator 95, the ratio between oxyhemoglobin and deoxyhemoglobin in the hemoglobin varies. In the HPLC apparatus 9, the blood sample is diluted, and the sample in a state in which oxygen content is relatively high is introduced into the analysis column 91. For this reason, 415 nm, which is the absorption maximum wavelength of oxyhemoglobin, is used as a measurement wavelength in a photometric mechanism 92. Therefore, in a case in which the ratio between oxyhemoglobin and deoxyhemoglobin varies, it is difficult to accurately measure the concentration of glycohemoglobin by using the absorption maximum wavelength of oxyhemoglobin.

Means for Solving the Problem

An object of the present invention is to appropriately prevent adverse effects caused by deterioration of the deaeration performance of the deaerator when using the deaerator continuously; for example, appropriately prevent deterioration of the measurement accuracy of a liquid chromatograph.

According to a first aspect of the present invention, there is provided a deaerator including: a liquid flow space; a reduced-pressure space; a gas permeable film that separates these spaces; and a pump for discharging a gas from within the reduced-pressure space to the outside, wherein the deaerator further includes a gas partial pressure variation suppression means for suppressing a variation in the partial pressure of a specific gas in the reduced-pressure space.

According to a second aspect of the present invention, there is provided a liquid chromatograph including: a column that holds a packing material; one or plural eluent holding parts each holding an eluent to be supplied to the column; and a deaerator for deaerating the eluent while the eluent is supplied from an eluent holding part to the column, wherein the deaerator further includes a gas partial pressure variation suppression means for suppressing a variation in the partial pressure of a specific gas in the reduced-pressure space.

The liquid chromatograph according to the present invention is configured so as to measure, for example, glycohemoglobin in a blood sample.

Preferably, the gas partial pressure variation suppression means is an oxygen partial pressure variation suppression means for suppressing a variation in the oxygen partial pressure of the reduced-pressure space.

The oxygen partial pressure variation suppression means is configured so as to introduce a gas from the exterior of the deaerator into the reduced-pressure space, for example, during deaeration. In this case, the oxygen partial pressure variation suppression means has, for example, a high pressure drop part for increasing transfer resistance against the gas to be introduced into the reduced-pressure space. The oxygen partial pressure variation suppression means further has, for example, an external air inlet for allowing the reduced-pressure space to communicate with the outside of the deaerator, and an external air introduction pipe connected to the external air inlet. In this case, the high pressure drop part is disposed, for example, at an intermediate portion or end portion of the external air introduction pipe. It is also permissible to provide the high pressure drop part at the external air inlet and omit the external air introduction pipe. The high pressure drop part includes, for example, a porous filter. A resistance tube (a pipe having a minute inner diameter (having a diameter of, for example, from 0.1 to 0.2 mm) formed in a spiral shape) may be used as the external air introduction pipe, so that the external air introduction pipe itself may serve as a high pressure drop part. A part of the external air introduction pipe may be formed of a resistance tube, so that the resistance tube may serve as the high pressure drop part.

The oxygen partial pressure variation suppression means may be configured to have an oxygen partial pressure detection part for monitoring the partial pressure of oxygen in the reduced-pressure space, and a valve that is disposed at an intermediate portion of the external air introduction pipe, and the open and closed state of the valve may be controlled based on a result of monitoring by the oxygen partial pressure detection part.

The deaerator according to the present invention has, for example, an exhaust outlet through which the reduced-pressure space communicates with the outside of the deaerator, and an exhaust pipe for discharging the gas inside the reduced-pressure space via the exhaust outlet, wherein a portion of the exhaust pipe extending between the exhaust outlet and the pump has high gas permeability. In this case, the oxygen partial pressure variation suppression means includes the portion of the exhaust pipe having high gas permeability. It is preferable that the exhaust pipe is formed from the same or substantially same material as that of the gas permeable film. In a case in which the gas permeable film is formed in a tubular shape, tubes formed from similar materials may be used as the gas permeable film and the exhaust pipe.

The deaerator according to the present invention further includes, for example, a branch pipe provided so as to branch from the exhaust pipe. It is preferable that the branch pipe has high gas permeability and is closed at an intermediate or end portion thereof. It is preferable that the branch pipe has a long length and a largest surface area possible.

The oxygen partial pressure variation suppression means in which the exhaust pipe and/or the branch pipe have high gas permeability is, for example, configured in such a manner that a valve is provided at an intermediate portion of the exhaust pipe, and that the valve is open during deaeration and is closed after completion of deaeration.

The deaerator according to the present invention may have: an exhaust outlet for allowing the reduced-pressure space to communicate with the outside of the deaerator; an exhaust sub-chamber for holding the gas drawn from the reduced-pressure space; and an exhaust pipe for connecting the exhaust outlet and the exhaust sub-chamber. In this case, the oxygen partial pressure variation suppression means is configured so as to return the gas in the exhaust sub-chamber to the reduced-pressure space after completion of deaeration. The oxygen partial pressure variation suppression means is, for example, configured in such a manner that the oxygen partial pressure variation suppression means includes a return pipe for returning the gas in the exhaust sub-chamber to the reduced-pressure space, and a valve provided at an intermediate portion of the return pipe, and that the valve is in the closed state during deaeration, but is opened after completion of deaeration so as to return the gas in the exhaust sub-chamber to the reduced-pressure space.

The oxygen partial pressure variation suppression means may be configured so as to open the reduced-pressure space to the atmosphere when the pump is not driven, and so as to open the reduced-pressure space to the atmosphere during driving of the pump only in a case in which a fixed condition is satisfied. In this case, the oxygen partial pressure variation suppression means is configured so as to, for example, open the reduced-pressure space to the atmosphere at fixed intervals or when the oxygen partial pressure of the reduced-pressure space becomes equal to or greater than a predetermined value.

The oxygen partial pressure variation suppression means may be configured so as to increase the degree of pressure reduction in the reduced-pressure space when the partial pressure of oxygen gas in the reduced-pressure space becomes equal to or greater than a predetermined value.

BRIEF DESCRIPTION OF THE DRAWINGS

FIG. 11 is a graph showing results of measurements of glycohemoglobin concentration in Example 1 and Comparative Example 2;

EXPLANATION OF SYMBOLS

Figure 1:
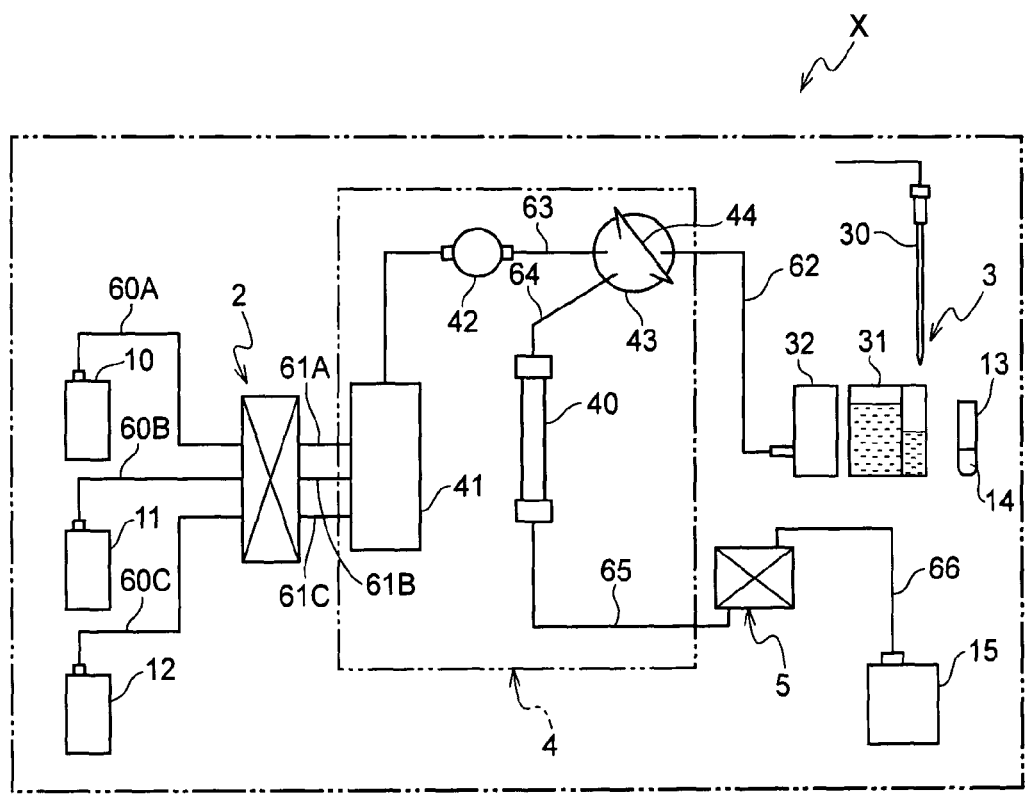
FIG. 1 is a schematic configuration diagram of an HPLC apparatus according to a first embodiment of the present invention.

X: HPLC apparatus (liquid chromatograph)
10, 11, 12: Eluent bottle (eluent holding part)
14: Blood sample
2, 7A, 7B, 7C, 7D, 7E, 7F, 7G: Deaerator
21A, 21B, 21C: Gas permeable tube (gas permeable film)
22: Pressure-reducing pump
23, 23A, 23B, 23C, 23A', 23B', 23C': High pressure drop part
23b: Filter (of high pressure drop part)
25A, 25B, 25C: Reduced-pressure space
25Aa, 25Ba, 25Ca: Exhaust outlet
25Ab, 25Bb, 25Cb: Atmospheric air inlet (external air inlet)
26A, 26B, 26C: Oxygen concentration measurement sensor (equivalent to oxygen partial pressure measurement part)
27A, 27B, 27C, 270: Exhaust pipe
271: Detection pipe (branch pipe)
274: Exhaust sub-chamber
275: Return pipe
276: Valve
28A, 28B, 28C: Atmospheric air introduction pipe
29A, 29B, 29C: Valve
40: Analysis column

BEST MODE FOR CARRYING OUT THE INVENTION

Hereinafter, first to eighth embodiments of the present invention will be described with reference to the drawings.

First, the first embodiment of the present invention will be described with reference to FIGS. 1 to 3.

Figure 2:
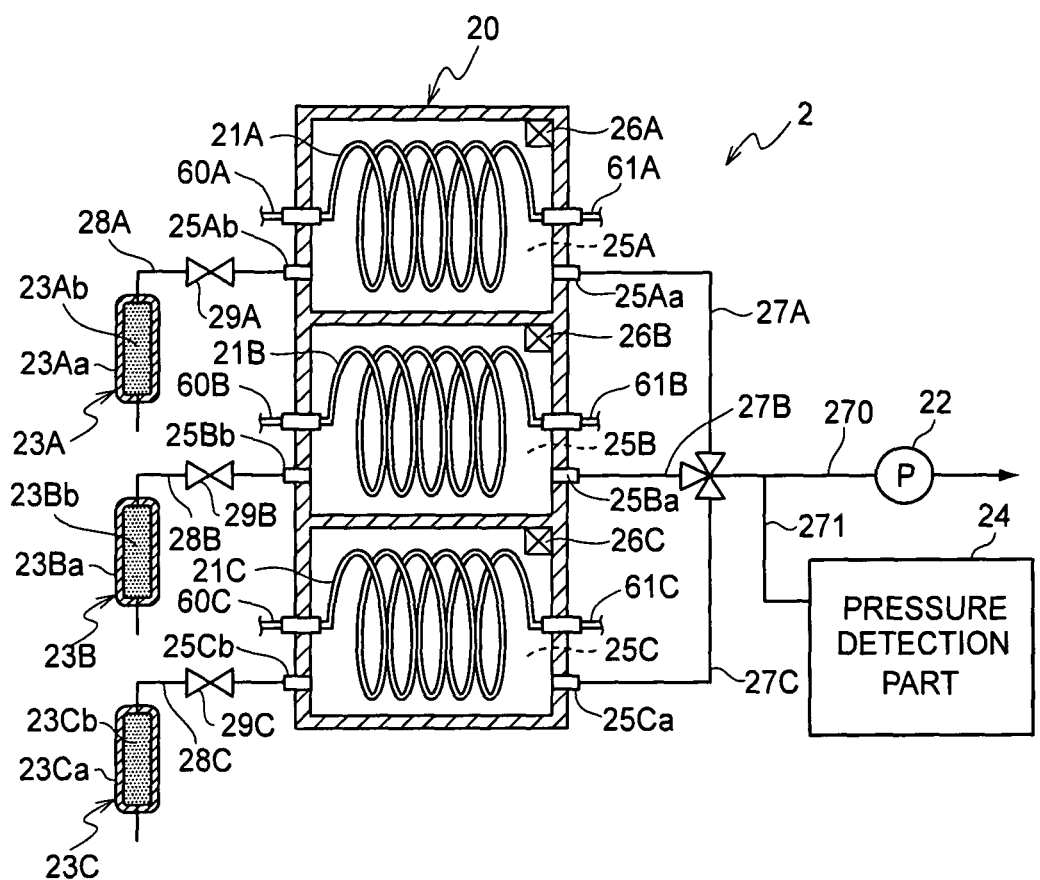
FIG. 2 is a sectional view schematically showing a part of the HPLC apparatus shown in FIG. 1 for explaining a deaerator.

An HPLC apparatus X shown in FIG. 1 is configured so as to measure the concentration of glycohemoglobin by using a whole blood, and the HPLC apparatus X is provided with plural eluent bottles 10, 11, and 12 (three in the drawing), a deaerator 2, a sample preparation unit 3, an analysis unit 4, and a photometric unit 5.

Respective eluent bottles 10, 11, and 12 hold eluents to be supplied to an analysis column 40 described below. As the eluents, buffers that are different in pH and/or salt concentration are used, for example.

The deaerator 2 is provided so as to remove dissolved gas from an eluent before supplying the eluent to the analysis unit 4 (the analysis column 40), and the deaerator 2 is connected to the eluent bottles 10, 11, and 12 by pipes 60A, 60B, and 60C and is connected to a manifold 41 of the analysis unit 4 by pipes 61A, 61B, and 61C. As shown in FIG. 2, the deaerator 2 has a chamber 20, plural gas permeable tubes 21A, 21B, and 21C (three in the drawing), a pressure-reducing pump 22, plural high pressure drop parts 23A, 23B, and 23C (three in the drawing), and a pressure detection part 24.

The chamber 20 is provided so as to define plural reduced-pressure spaces 25A, 25B, and 25C (three in the drawing), and accommodate the gas permeable tubes 21A, 21B, and 21C.

In the reduced-pressure spaces 25A, 25B, and 25C, oxygen concentration measurement sensors 26A, 26B, and 26C are arranged, and exhaust outlets 25Aa, 25Ba, and 25Ca and atmospheric air inlets 25Ab, 25Bb, and 25Cb are provided.

Oxygen concentration measurement sensors 26A, 26B, and 26C are provided so as to measure the concentration of oxygen in the reduced-pressure spaces 25A, 25B, and 25C. By measuring the concentration of oxygen in the reduced-pressure spaces 25A, 25B, and 25C by these oxygen concentration measurement sensors 26A, 26B, and 26C, it becomes possible to grasp a partial pressure of oxygen in the reduced-pressure spaces 25A, 25B, and 25C. As the oxygen concentration measurement sensors 26A, 26B, and 26C, various known sensors may be used.

Exhaust outlets 25Aa, 25Ba, and 25Ca are provided so as to discharge the gas from within the reduced-pressure spaces 25A, 25B, and 25C to the outside, and the exhaust outlets 25Aa, 25Ba, and 25Ca are connected to the pressure-reducing pump 22 via exhaust pipes 27A, 27B, 27C, and 270.

Atmospheric air inlets 25Ab, 25Bb, and 25Cb are provided so as to introduce atmospheric air into the reduced-pressure spaces 25A, 25B, and 25C, and atmospheric air introduction pipes 28A, 28B, and 28C are connected to these atmospheric air inlets 25Ab, 25Bb, and 25Cb. Valves 29A, 29B, and 29C are provided at intermediate portions of the atmospheric air introduction pipes 28A, 28B, and 28C. The valves 29A, 29B, and 29C are provided so as to allow selection between a state where atmospheric air is introduced into the reduced-pressure spaces 25A, 25B, and 25C and a state where atmospheric air is not introduced into the reduced-pressure spaces 25A, 25B, and 25C, and open/close states of the atmospheric air inlets 25Ab, 25Bb, and 25Cb are controlled by a control means (not shown in the drawing).

Plural high pressure drop parts 23A, 23B, and 23C are provided so as to absorb differences between the atmospheric pressure and the pressures of the reduced-pressure spaces 25A, 25B, and 25C. Specifically, when opening the valves 29A, 29B, and 29C, the high pressure drop parts 23A, 23B, and 23C serve to prevent rapid introduction of atmospheric air into the reduced-pressure spaces 25A, 25B, and 25C, and gradually increase the pressures of the reduced-pressure spaces 25A, 25B, and 25C by gradually introducing atmospheric air to the reduced-pressure spaces 25A, 25B, and 25C. These high pressure drop parts 23A, 23B, and 23C have configurations in which filters 23Ab, 23Bb, and 23Cb are contained inside sealed holders 23Aa, 23Ba, and 23Ca.

The sealed holders 23Aa, 23Ba, and 23Ca are formed in a hollow shape, and the insides thereof communicate with atmospheric air and the atmospheric air introduction pipes 28A, 28B, and 28C. The filters 23Ab, 23Bb, and 23Cb serve to provide resistance against a fluid when introducing atmospheric air into the reduced-pressure spaces 25A, 25B, and 25C. These filters 23Ab, 23Bb, and 23Cb are formed of a porous body with a pore diameter of, for example, from 10 to 150 μm. As a porous body in this case, various known porous bodies may be used if desired fluid resistance can be applied.

A pressure detection part 24 is provided so as to monitor the pressure (the degree of pressure reduction) of the reduced-pressure spaces 25A, 25B, and 25C, and the pressure detection part 24 communicates with an exhaust pipe 270 via a detection pipe 271, which is branched from an intermediate portion of the exhaust pipe 270, and the pressure detection part 24 communicates further with the reduced-pressure spaces 25A, 25B, and 25C.

The gas permeable tubes 21A, 21B, and 21C are provided so as to allow the eluents to flow therein and allows permeation of dissolved gas in the eluents. The gas permeable tubes 21A, 21B, and 21C are formed in a hollow shape and formed of a known gas permeable film such as of a silicon resin or polytetrafluoroethylene. Due to the spiral shapes of the gas permeable tubes 21A, 21B, and 21C, long flow channel lengths within the reduced-pressure spaces 25A, 25B, and 25C are ensured, large areas of contact with gas in the reduced-pressure spaces 25A, 25B, and 25C are ensured, and long retention times of the eluents in the reduced-pressure spaces 25A, 25B, and 25C are ensured.

The pressure-reducing pump 22 is provided so as to draw the gas from the reduced-pressure spaces 25A, 25B, and 25C via the exhaust pipes 27A, 27B, 27C, and 270 and so as to reduce the pressure of the reduced-pressure spaces 25A, 25B, and 25C. Turning-on and off of the pressure-reducing pump 22 is controlled by a control means (not shown in the drawing). The control means controls turning on and off of the pressure-reducing pump 22 based on, for example, whether or not the deaerator 2 is driven. Also during driving of the deaerator 2, the control means controls turning on and off of the pressure-reducing pump 22 when the pressure (the degree of pressure reduction) of the reduced-pressure spaces 25A, 25B, and 25C detected by the pressure detection part 24 deviates from a predetermined value range.

As shown in FIG. 1, the sample preparation unit 3 is provided so as to prepare a sample to be introduced into an analysis column 40, from blood cell components sampled from the blood collection tube 13. The sample preparation unit 3 has a sampling nozzle 30, a preparation liquid tank 31, and a dilution tank 32.

The sampling nozzle 30 is provided so as to sample various liquids such as a blood sample 14 in the blood collection tube 13, and the sampling nozzle 30 is capable of suctioning and ejecting liquid and movable in the vertical direction and the horizontal direction. The operation of the sampling nozzle 30 is controlled by a control means (not shown in the drawing).

The preparation liquid tank 31 holds a preparation liquid for preparing, from the blood sample 14, a sample for introduction to be introduced into the analysis column 40. In the preparation liquid tank 31, a hemolytic liquid for hemolyzing red blood cells, a diluent for diluting the hemolytic liquid, and the like are held as preparation liquids.

The dilution tank 32 is provided so as to provide a site for preparing a sample for introduction by hemolyzing red blood cells in the blood sample 14 and diluting the hemolytic liquid. The dilution tank 32 is configured in such a manner that the dilution tank 32 is connected to an injection valve 43 in the below-described analysis unit 4 via a pipe 62, and that a sample for introduction, which has been prepared in the dilution tank 32, can be introduced into the analysis column 40 via the injection valve 43.

The analysis unit 4 is provided so as to control adsorption of biogenic substances onto the packing material of the analysis column 40 and desorption of biogenic substances from the packing material, thereby delivering various biogenic substances to the photometric unit 5. The temperature of the analysis unit 4 is controlled by a temperature adjusting mechanism (not shown in the drawing). The temperature set in the analysis unit 4 is, for example, about 40° C. The analysis column 40 holds a packing material for selectively adsorbing the hemoglobin in the sample. As a packing material, a methacrylic ester copolymer, for example, is used.

The analysis unit 4 has a manifold 41, a liquid feed pump 42, and an injection valve 43, as well as the analysis column 40.

The manifold 41 is provided so as to allow an eluent to be selectively supplied from a specific eluent bottle 10, 11, or 12 among the plural eluent bottles 10, 11, and 12, to the injection valve 43. The manifold 41 is connected to the reduced-pressure spaces 25A, 25B, and 25C of the deaerator 2 (the gas permeable tubes 21A, 21B, and 21C) via the pipes 61A, 61B, and 61C, and is connected to the injection valve 43 via a pipe 63.

The liquid feed pump 42 is provided so as to provide a power for moving the eluent to the injection valve 43, and is provided at an intermediate portion of the pipe 63. The liquid feed pump 42 is operated such that the feed rate of the eluent is, for example, in the range of 1.0 to 2.0 ml/min.

The injection valve 43 takes a fixed amount of a sample for introduction and enables the sample for introduction to be introduced into the analysis column 40. The injection valve 43 is provided with plural introduction ports and discharge ports (not shown in the drawing). An injection loop 44 is connected to the injection valve 43. The injection loop 44 is capable of holding a fixed amount (for example, several μL) of liquid. Switching of the injection valve 43 according to the occasion enables selection between (i) a state in which the injection loop 44 communicates with the dilution tank 32 and the sample for introduction is supplied from the dilution tank 32 to the injection loop 44, (ii) a state in which the injection loop 44 communicates with the analysis column 40 via the pipe 64 and the sample for introduction is introduced from the injection loop 44 to the analysis column 40, or (iii) a state in which a cleaner liquid is supplied from a cleaner tank (not shown in the drawing) to the injection loop 44. As such an injection valve 43, for example, a hexagonal valve may be used.

Figure 3:
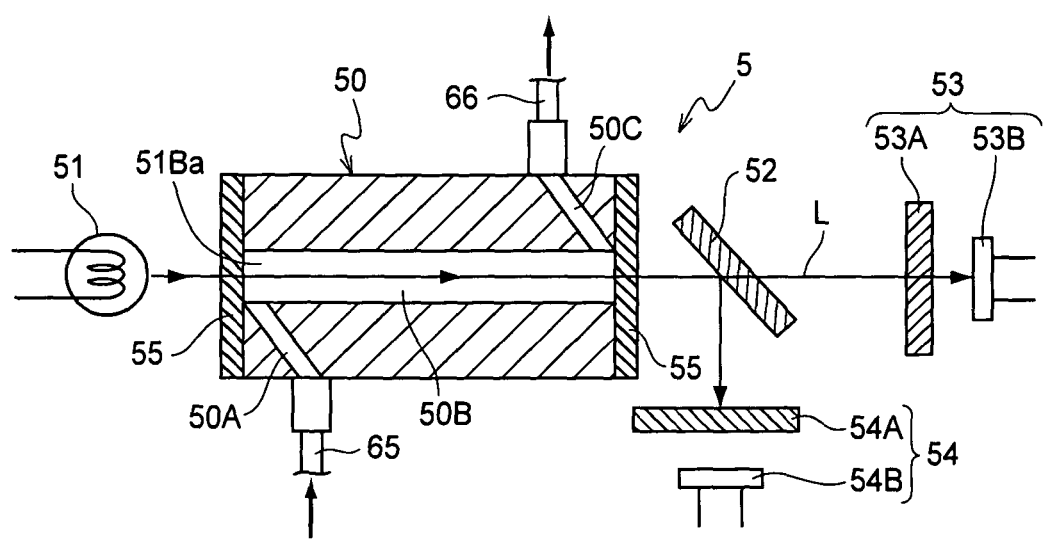
FIG. 3 is a sectional view for explaining a photometric unit in the HPLC apparatus shown in FIG. 1.

As shown in FIG. 3, the photometric unit 5 is provided so as to optically detect hemoglobin contained in a desorption liquid from the analysis column 40. The photometric unit 5 has a photometric cell 50, a light source 51, a beam splitter 52, a light receiving system for measurement 53, and a light receiving system for reference 54.

The photometric cell 50 is provided so as to define the photometric area. The photometric cell 50 has an introduction flow channel 50A, a photometric flow channel 50B, and a discharge flow channel 50C, and these flow channels 50A, 50B, and 50C communicate with each other in series. The introduction flow channel 50A is provided so as to introduce the eluate from the analysis column 40 (see FIG. 2) into the photometric flow channel 50B, and the introduction flow channel 50A is connected to the analysis column 40 via the pipe 65. The photometric flow channel 50B allows the eluate, which is to be measured by photometry, to flow therethrough, and provides a site at which the eluate is photometrically measured. The photometric flow channel 50B is linearly formed. The photometric flow channel 50B has openings at both ends, and both end portions of the photometric flow channel 50B are covered with transparent covers 55. The discharge flow channel 50C is provided so as to discharge the eluate in the photometric flow channel 50B. The discharge flow channel 50C is connected to a waste liquid tank 15 via the pipe 66 (see FIG. 2).

A light source 51 is provided so as to irradiate the eluate flowing through the photometric flow channel 50B with light. The light source 51 is disposed to face an end face 50Ba (the transparent cover 55) of the photometric flow channel 50B such that the optical axis L passes through the center of the photometric flow channel 50B. The light source 51 used is a light source capable of emitting light in a wavelength range including light having a wavelength 415 nm, which is the absorption maximum wavelength of oxyhemoglobin, and light having a reference wavelength of 500 nm, and is, for example, a halogen lamp. Of course, a light source other than halogen lamps, such as a light source having one or plural LED devices, may be used as the light source 51.

A beam splitter 52 is provided so as to divide the light that has passed through the photometric flow channel 50B among the lights emitted from the light source 51, and allow the divided lights to enter the light receiving system for measurement 53 and the light receiving system for reference 54. The beam splitter 52 is disposed at the optical axis L, at an inclination of 45 degrees. As the beam splitter 52, various known beam splitters such as a half mirror may be used.

The light receiving system for measurement 53 is provided so as to selectively receive 415 nm light, which is the absorption maximum wavelength of oxyhemoglobin, contained in the light that has passed through the beam splitter 52, and the light receiving system for measurement 53 is disposed on the optical axis L. The light receiving system for measurement 53 has an interference filter 53A for selectively passing 415 nm light and a light receiving device 53B for receiving light that has passed through the interference filter 53A. A photo diode may be used as the light receiving device 53B.

The light receiving system for reference 54 selectively receives 500 nm light, which is a reference wavelength, contained in the light of which the light path has been changed by reflection at the beam splitter 52. The light receiving system for reference 54 has an interference filter 54A for selectively passing 500 nm light and a light receiving device 54B for receiving the light that has passed through the interference filter 54A. A photo diode may be used as the light receiving device 54B.

Next, the operation of the HPLC apparatus X is described.

In the HPLC apparatus X, when the instruction to start the measurement has been confirmed, the blood sample 14 is sampled from the blood collection tube 13. The instruction to start the measurement is effected by operation of a predetermined operational button of the HPLC apparatus X (not shown in the drawings) by a user. Sampling of the blood sample 14 from the blood collection tube 13 is carried out by operating the sampling nozzle 30.

The blood sample 14 that has been sampled by the sampling nozzle 30 is supplied to the dilution tank 32 by operating the sampling nozzle 30. Further, a hemolytic agent and a diluent are sequentially supplied from the preparation liquid tank 31 to the dilution tank 32, and the liquid in the dilution tank 32 is mixed by pipetting treatment using the sampling nozzle 30, as a result of which a sample for introduction is prepared.

Further, in the HPLC apparatus X, when the instruction to start the measurement has been confirmed, the eluent is supplied to the injection valve 43. The eluent is supplied from the eluent bottles 10, 11, or 12 to the injection valve 43 via the deaerator 2 and the manifold 41, by a power of the liquid feed pump 42. In addition, the eluent bottle (10, 11, or 12) from which the eluent is supplied, among plural eluent bottles 10, 11, and 12, is selected by controlling the manifold 41.

In the deaerator 2, after the eluent has flowed through the gas permeable tube 21A, 21B, or 21C inside the reduced-pressure space 25A, 25B, or 25C, the eluent is discharged from the gas permeable tube 21A, 21B, or 21C. In this case, since the gas permeable tubes 21A, 21B, and 21C are formed from a material having high gas permeability and the pressure of the reduced-pressure spaces 25A, 25B, and 25C is reduced by the pressure-reducing pump 22, dissolved gas containing dissolved oxygen is removed from the eluent while the eluent flows through the gas permeable tube 21A, 21B, or 21C.

In the deaerator 2, the oxygen concentrations in the reduced-pressure spaces 25A, 25B, and 25C are monitored by the oxygen concentration measurement sensors 26A, 26B, and 26C. Monitoring of the oxygen concentration by the oxygen concentration measurement sensors 26A, 26B, and 26C may be continuously carried out or may be intermittently carried out. In the case of intermittently monitoring the concentration of oxygen, timing of measuring the concentration of oxygen is such that the oxygen concentration is measured at fixed intervals determined in advance or every time measurements of a fixed number of blood samples are completed.

The monitoring results by these oxygen concentration measurement sensors 26A, 26B, and 26C are outputted to a control means (not shown in the drawing), and opening and closing of each of the valves 29A, 29B, and 29C is separately controlled by the control means.

More specifically, for example, in a case in which the result of the measurement of the oxygen concentration by the oxygen concentration measurement sensors 26A, 26B, or 26C is higher than a predetermined first threshold value (for example, equivalent to approximately 40% by volume in terms of oxygen concentration), the control means opens the valves 29A, 29B, or 29C corresponding to the reduced-pressure space 25A, 25B, or 25C that has exceeded the first threshold. Thereby, atmospheric air is introduced into the reduced-pressure space 25A, 25B, or 25C, via the atmospheric air introduction pipe 28A, 28B, or 28C, and the atmospheric air inlet 25b, 25Bb, or 25Cb. In this case, since the high pressure drop parts 23A, 23B, and 23C are provided at intermediate portions of the atmospheric air introduction pipes 28A, 28B, and 28, atmospheric air is gradually introduced into the reduced-pressure space 25A, 25B, or 25C, and pressure of the reduced-pressure space 25A, 25B, or 25C gradually increases. As a result, the oxygen partial pressure of the reduced-pressure spaces 25A, 25B, or 25C is gradually decreased due to introduction of atmospheric air.

On the other hand, when the oxygen concentration has become lower than a predetermined second threshold value (for example, equivalent to approximately 20% by volume in terms of oxygen concentration), the control means closes the valve 29A, 29B, or 29C. The closing of the valve 29A, 29B, or 29C may be unconditionally carried out after a predetermined time has passed since opening of the valve 29A, 29B, or 29C irrespective of the result of the measurement of the oxygen concentration by the oxygen concentration measurement sensor 26A, 26B, or 26C.

In a case in which opening and closing of the valves 29A, 29B, and 29C are controlled in this way, it is possible to maintain the partial pressures of oxygen in the reduced-pressure spaces 25A, 25B, and 25C in a predetermined range, for example, between the first threshold value and the second threshold value. Therefore, the oxygen partial pressures of the reduced-pressure spaces 25A, 25B, and 25C are prevented from unduly increasing to largely exceed the first threshold value. As a result, in the deaerator 2, a decrease in the amount of gas, such as oxygen, that can be transferred from the eluent within the gas permeable tubes 21A, 21B, and 21C to the reduced-pressure spaces 25A, 25B, and 25C can be suppressed. Therefore, in the deaerator 2, a decrease in the deaeration performance due to an increase of the partial pressure of the deaeration gas, such as oxygen, can be suppressed even when deaeration of the eluent is continuously carried out. If the partial pressures of oxygen in the reduced-pressure spaces 25A, 25B, and 25C can be maintained in a fixed range, generation of variations in the degree of deaeration of the eluent (variations in the amount of dissolved oxygen) is suppressed, and the composition of dissolved gas, such as the concentration of dissolved oxygen, in the eluent can be uniformized.

In particular, if the high pressure drop parts 23A, 23B, and 23C are provided so as to allow atmospheric air to be gradually introduced into the reduced-pressure spaces 25A, 25B, and 25C, the oxygen partial pressures of the reduced-pressure spaces 25A, 25B, and 25C can be maintained in a predetermined range more reliably and more simply. If the high pressure drop parts 23A, 23B, and 23C are provided, the difference between the first threshold value and the second threshold value, which are target values of the control of the oxygen partial pressure, can be made smaller, and variations in the oxygen partial pressure can be restricted to be in a smaller range.

The eluent discharged from the reduced-pressure space 25A, 25B, or 25C (the gas permeable tube 21A, 21B, or 21C) is supplied to the manifold 41 via the pipe 61A, 61B, or 61C, and then the eluent is introduced into the injection valve 43 via the pipe 64.

The eluent supplied to the injection valve 43 is supplied to the analysis column 40 via the pipe 65. By carrying out a switching operation of the injection valve 43, a sample for introduction in the injection loop 44 is introduced, together with the eluent, into the analysis column 40. When a predetermined time has passed since the initiation of the introduction of the sample for introduction, a switching operation of the injection valve 43 is carried out, whereby the eluent is continued to be supplied to the analysis column 40 and the injection loop 44 is cleaned. At the same time as the cleaning of the injection loop 44, a sample for introduction is prepared, in the same manner as that described above, from a blood sample 14 of another blood collection tube 13 than the previous one, and, after the cleaning of the injection loop 44, the sample for introduction is introduced again into the injection loop 44. Such preparation, introduction, and cleaning of a sample for introduction are repeatedly carried out in accordance with the number of blood collection tubes 13 (blood samples 14) to be measured, during which the injection valve 43 is switched according to the occasion.

As a result of the introduction of the sample for introduction into the analysis column 40, glycohemoglobin is adsorbed on the packing material. After allowing glycohemoglobin to be adsorbed on the packing material, the kind of the eluent to be supplied to the analysis column 40 is changed by the manifold 41 according to the occasion, thereby allowing glycohemoglobin, which is adsorbed on the packing material, to be desorbed.

As described above, the eluent that has passed through the deaerator 2 has a uniformized concentration of dissolved oxygen, so that the eluent to be supplied to the analysis column 40 also has a uniformized concentration of dissolved oxygen. As a result, in a case in which hemoglobin is desorbed from the packing material and discharged from the analysis column 40 together with the eluent, the ratio between oxyhemoglobin and deoxyhemoglobin in the hemoglobin in the eluate is uniformized. In addition, even in the case of measuring glycohemoglobin in plural blood samples 14, the different blood samples have mutually uniformized ratios between oxyhemoglobin and deoxyhemoglobin in the hemoglobin in the eluate.

The desorption liquid containing glycohemoglobin and discharged from the analysis column 40 is supplied to the photometric cell 50 of the photometric unit 5 via the pipe 66. The desorption liquid is introduced into the photometric cell 50 via the pipe 66 and the introduction flow channel 50A. After passing through the photometric flow channel 50B and the discharge flow channel 50C, the desorption liquid is introduced into the waste liquid tank 15 via the pipe 66.

In the photometric unit 5, when the eluate passes through the photometric flow channel 50B, the eluate is continuously irradiated with light from the light source 51. The light that has passed through the photometric flow channel 50B is divided by the beam splitter 52, and then the light is received by the light receiving system for measurement 53 and the light receiving system for reference 54. In the light receiving system for measurement 53, light of 415 nm, the absorption maximum wavelength of oxyhemoglobin, that has passed through the interference filter 53A is selectively received in the light receiving device 53B. On the other hand, in the light receiving system for reference 54, light of the reference wavelength, 500 nm, that has passed through the interference filter 54A is selectively received in the light receiving device 54B.

The result of light reception by the light receiving devices 53B and 54B are outputted to an operation circuit (not shown in the drawing), and the chromatogram of hemoglobin and the concentration of glycohemoglobin (the ratio of glycohemoglobin to the total amount of hemoglobin) are calculated by the operation circuit. The result of the calculation by the operation circuit is displayed on a display panel (not shown in the drawing), and is printed out automatically or when button operation is carried out by the user.

In the HPLC apparatus X, since the ratio between oxyhemoglobin and deoxyhemoglobin in the eluate is uniformized over one measurement, inaccuracy of measurement results caused by variations of the amount of dissolved oxygen during measurement can be reduced. In addition, in a case in which measurements of plural blood samples are consecutively carried out, since the ratio between oxyhemoglobin and deoxyhemoglobin in the eluate is uniformized in each measurement, variations in measurement results between plural measurements can be suppressed.

Further, even in a case in which the reduced-pressure spaces 25A, 25B, and 25C are opened to the atmosphere when driving of the deaerator 2 has been stopped, the oxygen partial pressures of the reduced-pressure spaces 25A, 25B, and 25C before stopping the apparatus are maintained in a fixed range that is not greatly different from the oxygen partial pressure in the atmosphere. Therefore, the oxygen partial pressure when the deaerator 2 is driven again is not greatly different from the oxygen partial pressure when the deaerator 2 is driven continuously. Accordingly, the difference, in the dissolved amount of gas components (for example, the amount of dissolved oxygen) included in the eluent, between an initial stage of driving of the deaerator 2 and after driving the deaerator 2 for a certain time can be decreased. As a result, measurement errors between a blood sample 14 analyzed at the initial stage of driving of the deaerator 2 and a blood sample 14 analyzed after driving the deaerator 2 for a certain time can be decreased, and measurement accuracy can be improved.

Further, the deaerator 2 may be configured in such a manner that the oxygen concentration measurement sensors 26A, 26B, and 26C are omitted, and that the valves 29A, 29B, and 29C are opened at fixed time intervals or every time measurements of a fixed number of samples are completed, thereby intermittently introducing atmospheric air into the reduced-pressure spaces 25A, 25B, and 25C.

Next, deaerators according to second to eighth embodiments of the present invention are described with reference to FIGS. 4 to 10. In the drawings referred to in the below, the same members and the same elements as in the deaerator 2 according to the first embodiment of the present invention are designated by the same reference characters, and duplicated explanations thereof are omitted.

Figure 4:
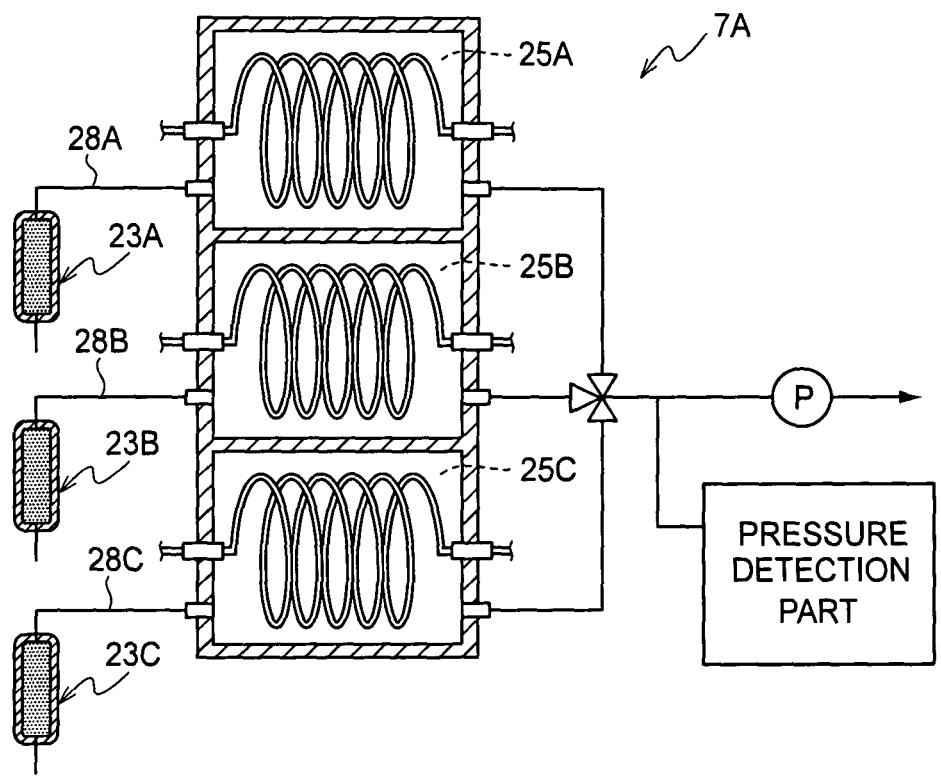
FIG. 4 is a sectional view corresponding to FIG. 2 for explaining a deaerator according to a second embodiment of the present invention.

In FIG. 4, a deaerator 7A according to the second embodiment of the present invention is illustrated. The deaerator 7A is a deaerator in which the oxygen concentration measurement sensors 26A, 26B, and 26C and the valves 29A, 29B, and 29C (see FIG. 2) in the deaerator 2 according to the first embodiment are omitted.

In the deaerator 7A, atmospheric air is allowed to gradually and naturally flow into the reduced-pressure spaces 25A, 25B, and 25C via the high pressure drop parts 23A, 23B, and 23C and the atmospheric air introduction pipes 28A, 28B, and 28C. Therefore, atmospheric air is always introduced into the reduced-pressure spaces 25A, 25B, and 25C, so that increases in the oxygen partial pressures in the reduced-pressure spaces 25A, 25B, and 25C can be suppressed. In addition, in the deaerator 7A, the oxygen concentration measurement sensors 26A, 26B, and 26C and the valves 29A, 29B, and 29C are unnecessary, and control of the valves 29A, 29B, and 29C (see FIG. 2) is unnecessary, so that the deaerator 7A has an advantage both in manufacturing cost and running cost.

Figure 5:
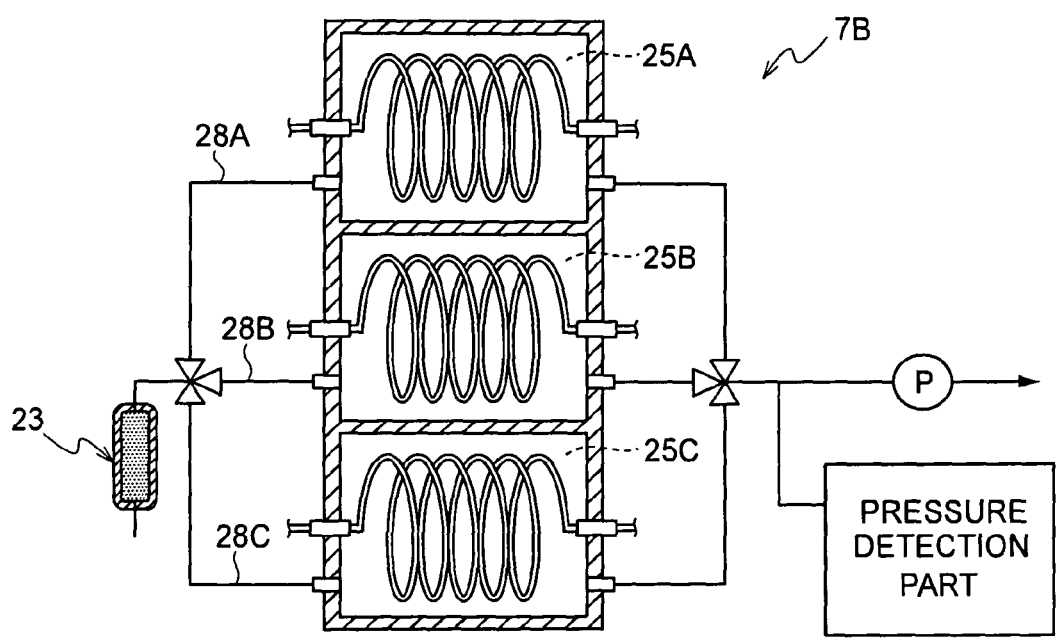
FIG. 5 is a sectional view corresponding to FIG. 2 for explaining a deaerator according to a third embodiment of the present invention.

In FIG. 5, a deaerator 7B according to a third embodiment of the present invention is illustrated. The deaerator 7B is configured in such a manner that one high pressure drop part 23 applies inflow resistance against the atmospheric air to be introduced into the reduced-pressure spaces 25A, 25B, and 25C in deaerator 7A (see FIG. 4) according to the second embodiment.

Since the deaerator 7B requires only one high pressure drop part 23, the deaerator 7B has a further advantage in terms of manufacturing cost.

Figure 6:
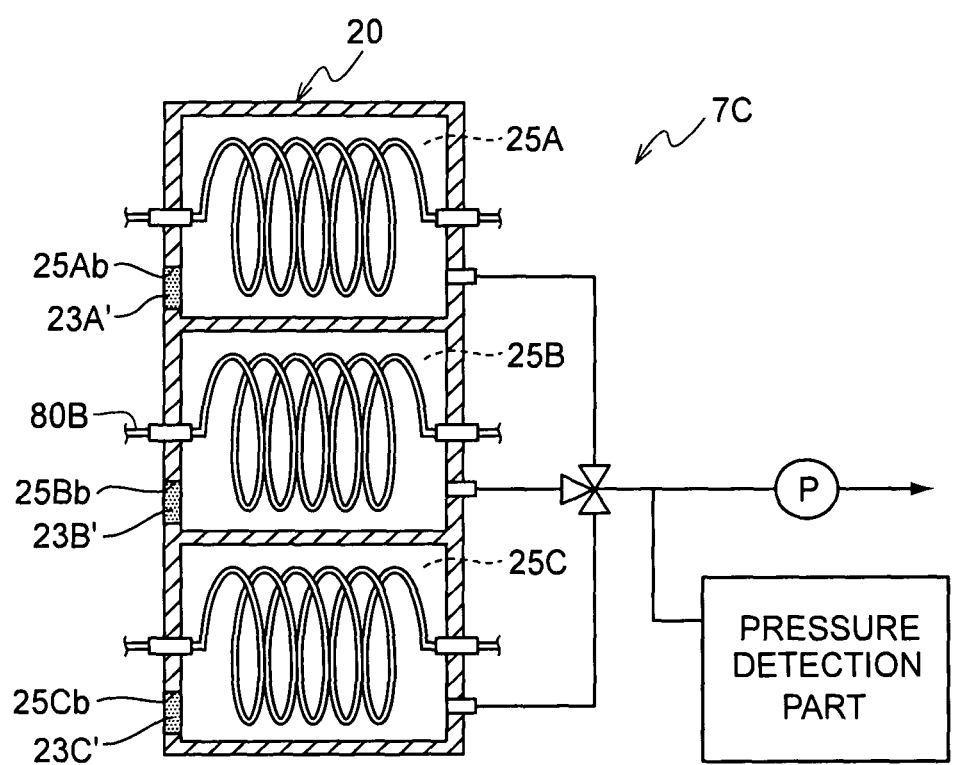
FIG. 6 is a sectional view corresponding to FIG. 2 for explaining a deaerator according to a fourth embodiment of the present invention.

In FIG. 6, a deaerator 7C according to a fourth embodiment of the present invention is shown. In the deaerator 7C, high pressure drop parts 23A', 23B', and 23C' are arranged at the atmospheric air inlets 25Ab, 25Bb, and 25Cb in the reduced-pressure spaces 25A, 25B, and 25C. The high pressure drop parts 23A', 23B', and 23C' are formed of, for example, a known porous body.

In the deaerator 7C, since atmospheric air is allowed to gradually and naturally flow into the reduced-pressure spaces 25A, 25B, and 25C via the high pressure drop parts 23A', 23B', and 23C', increases of the oxygen partial pressures of the reduced-pressure spaces 25A, 25B, and 25C can be suppressed. In addition, in the deaerator 7C, the oxygen concentration measurement sensors 26A, 26B, and 26C, the atmospheric air introduction pipes 28A, 28B, and 28C, and the valves 29A, 29B, and 29C (see FIG. 2) can be omitted, so that the deaerator 7C has an advantage in both manufacturing cost and running cost.

Further, in the deaerator 7C, in place of arranging the high pressure drop parts 23A', 23B', and 23C' at the atmospheric air inlets 25Ab, 25Bb, 25Cb, at least a part of the chamber 20 may be formed to be porous, or one or plural minute holes communicating with the reduced-pressure spaces 25A, 25B, and 25C may be formed at a part of the chamber 20, so as to allow the atmospheric air to naturally flow into the reduced-pressure spaces 25A, 25B, and 25C. In place of arranging the high pressure drop parts 23A', 23B', and 23C' at the atmospheric air inlets 25Ab, 25Bb, 25Cb, the deaerator 7C may be configured in such a manner that valves are provided at the atmospheric air inlets 25Ab, 25Bb, 25Cb so as to introduce the atmospheric air into the reduced-pressure spaces 25A, 25B, and 25C by opening and closing of the valves.

In the deaerator 7C, the high pressure drop part 23 may be omitted, and resistance tubes (pipes having a minute inner diameter (for example, a diameter of from 0.1 to 0.2 mm) formed in a spiral shape) may be adopted as the atmospheric air introduction pipes 28A, 28B, and 28C, such that the external air introduction pipes 28A, 28B, and 28C themselves serve as high pressure drop parts. A part of each external air introduction pipe may be formed of a resistance tube, so that the resistance tube can be used also as a high pressure drop part. Such a configuration in which the resistance tube is used can be applied also to the first to third deaerators 2, 7A, and 7B (FIGS. 2, 4, and 5) according to the present invention.

Figure 7:
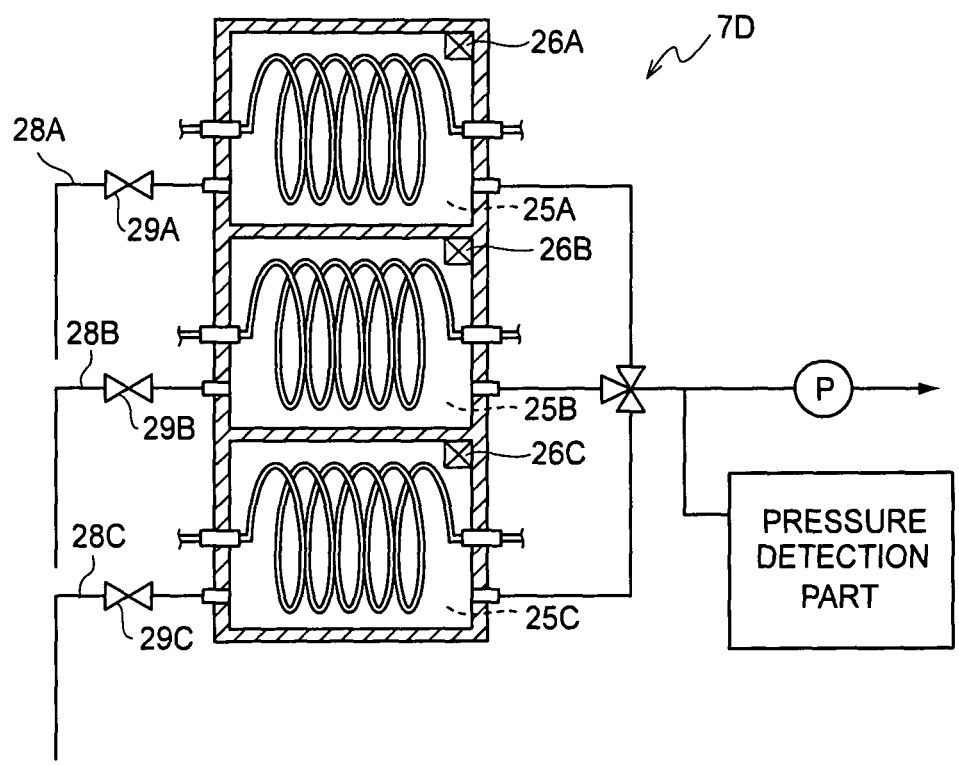
FIG. 7 is a sectional view corresponding to FIG. 2 for explaining a deaerator according to a fifth embodiment of the present invention.

In FIG. 7, a deaerator 7D according to a fifth embodiment of the present invention is shown. In the deaerator 7D, the high pressure drop parts 23A, 23B, and 23C (see FIG. 2) in the deaerator 2 according to the first embodiment are omitted. Specifically, the deaerator 2 is configured in such a manner that the oxygen concentration measurement sensors 26A, 26B, and 26C monitors the oxygen concentrations (oxygen partial pressures) of the reduced-pressure spaces 25A, 25B, and 25C, and that, when the oxygen concentration (oxygen partial pressure) of the reduced-pressure space 25A, 25B, or 25C becomes equal to or greater than a fixed value, the valve 29A, 29B, or 29C is opened to introduce the atmospheric air into the reduced-pressure space 25A, 25B, or 25C via the atmospheric air introduction pipe 28A, 28B, or 28C.

In the deaerator 7D, the atmospheric air is introduced into the reduced-pressure space 25A, 25B, or 25C when the oxygen concentration (the oxygen partial pressure) of the reduced-pressure space 25A, 25B, or 25C becomes high, as a result of which the oxygen partial pressure can be decreased (so as to be closer to that of the atmosphere). In addition, the deaerator 7D has an advantage in a manufacturing cost due to omission of the high pressure drop parts 23A, 23B, and 23C (see FIG. 2).

In the deaerator 7D, the oxygen concentration measurement sensors 26A, 26B, and 26C may be omitted, and the valves 29A, 29B, and 29C may be opened at fixed intervals or every time measurements of a fixed number of samples are completed, thereby intermittently introducing the atmospheric air into the reduced-pressure spaces 25A, 25B, and 25C.

Figure 8:
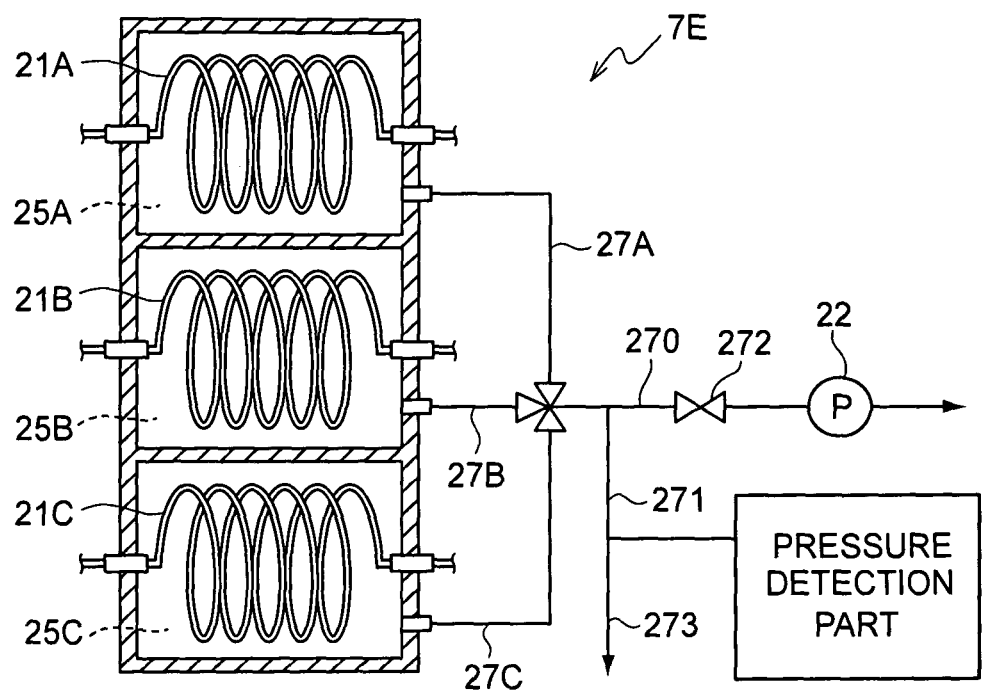
FIG. 8 is a sectional view corresponding to FIG. 2 for explaining a deaerator according to a sixth embodiment of the present invention.

In FIG. 8, a deaerator 7E according to a sixth embodiment of the present invention is shown. The deaerator 7E is different from the deaerator 2 according to the first embodiment (see FIG. 2), in the means for uniformizing the oxygen partial pressures of the reduced-pressure spaces 25A, 25B, and 25C. Specifically, the high pressure drop parts 23A, 23B, and 23C, the oxygen concentration measurement sensors 26A, 26B, and 26C, the atmospheric air inlets 25Ab, 25Bb, and 25Cb, and the atmospheric air introduction pipes 28A, 28B, and 28C (see FIG. 2), which are provided in the deaerator 2 described above, are omitted in the deaerator 7E.

In the deaerator 7E, the exhaust pipes 27A, 27B, 27C, and 270 and the detection pipe 271 have high gas permeability. As a material for the exhaust pipes 27A, 27B, 27C, and 270 and the detection pipe 271, the same material as that of the gas permeable tubes 21A, 21B, and 21C, for example a material formed of a silicon resin or polytetrafluoroethylene, may be used. It is preferable that the detection pipe 271 is a long pipe and has a large surface area. In the deaerator 7E, a valve 272 is provided at an intermediate portion of the exhaust pipe 270. The end portion of the detection pipe 271 is closed by an airtight stopper 273. The valve 272 is set in the closed state when the deaerator 7E is not driven, while the valve 272 is set in the open state when the deaerator 7E is driven, by the control means (not shown in the drawing).

In the deaerator 7E, during driving, the inner pressures of the exhaust pipes 27A, 27B, 27C, and 270 and the detection pipe 271 are made as low as those of the reduced-pressure spaces 25A, 25B, and 25C, and the gases of the reduced-pressure spaces 25A, 25B, and 25C are discharged via these pipes 27A, 27B, and 27C, 270, and 271. On the other hand, when the deaerator 7E is not driven, the valve 272 is closed, so that the pipes 27A, 27B, 27C, 270, and 271 are in a reduced-pressure state, similarly to the reduced-pressure spaces 25A, 25B, and 25C. Therefore, atmospheric air is gradually introduced into the reduced-pressure spaces 25A, 25B, and 25C via the pipes 27A, 27B, 27C, 270, and 271 until the pressures of the reduced-pressure spaces 25A, 25B, and 25C become approximately the same as the atmospheric pressure. In particular, in a case in which the pipes 27A, 27B, 27C, 270, and 271 are formed from a silicon resin, air with a high oxygen proportion is introduced into the reduced-pressure spaces since oxygen is more permeable through the silicon resin than nitrogen. Therefore, the oxygen partial pressures of the reduced-pressure spaces 25A, 25B, and 25C when the deaerator 7E is not driven can be made more closer to those when the deaerator 7E is driven. As a result, differences in the oxygen partial pressures of the reduced-pressure spaces 25A, 25B, and 25C between when the deaerator 7E is driven and after a certain time has passed since the deaerator 7E is stopped can be decreased. In other words, the oxygen partial pressures in the reduced-pressure spaces 25A, 25B, and 25C at an initial stage of driving of the deaerator 7E can be made approximately the same as the oxygen partial pressures in the reduced-pressure spaces 25A, 25B, and 25C after the deaerator 7E has been driven for a certain time. Thereby, it is possible to suppress variations in the oxygen partial pressures in the reduced-pressure spaces 25A, 25B, and 25C since the initial stage of driving of the deaerator 7E until the certain time has passed thereafter.

In the case in which the exhaust pipes 27A, 27B, 27C, and 270 and the detection pipe 271 are formed from the same material as that of the gas permeable tubes 21A, 21B, and 21C, external air can be introduced into the reduced-pressure spaces 25A, 25B, and 25C after the operation of the deaerator 7E is stopped, in a state similar to the state during driving of the deaerator 7E. In other words, in both of when the deaerator 7E is driven and when the deaerator 7E is not driven, the pressure reduction degrees of the reduced-pressure spaces 25A, 25B, and 25C are decreased (so as to be closer to the atmospheric pressure) in order to prevent variations of the oxygen partial pressure (the oxygen concentration) from becoming large, and the eluents remaining inside the gas permeable tubes 21A, 21B, and 21C can be inhibited from being condensed.

Further, in a case in which a pipe with a long pipe length is used as the detection pipe 271, a surface area of the detection pipe 271 is ensured, so that the pressure reduction degrees of the reduced-pressure spaces 25A, 25B, and 25C after the operation of the deaerator 7E is stopped can be decreased more rapidly. Thereby, the eluents remaining inside the gas permeable tubes 21A, 21B, and 21C are inhibited from being condensed.

In the deaerator 7E, the valve 272 may be intermittently closed during continuous driving of the deaerator 7E. In this case, the oxygen concentration (the oxygen partial pressure) of the reduced-pressure spaces 25A, 25B, and 25C may be monitored, and the valve 272 may be closed when the oxygen concentration (the oxygen partial pressure) exceeds a predetermined threshold value, or may be closed at fixed intervals.

It is not essential that the detection pipe 271 be closed by the airtight stopper 273, and air tightness inside the detection pipe 271 may be maintained by, for example, tying a part of the detection pipe 271.

Further, in the deaerator 7E, the valve 272 provided at an intermediate portion of the exhaust pipe 270 may be omitted, and air tightness inside the exhaust pipe 270 when the deaerator 7E (the pressure-reducing pump 22) is not driven may be ensured using a check valve that the pressure-reducing pump 22 has.

Figure 9:
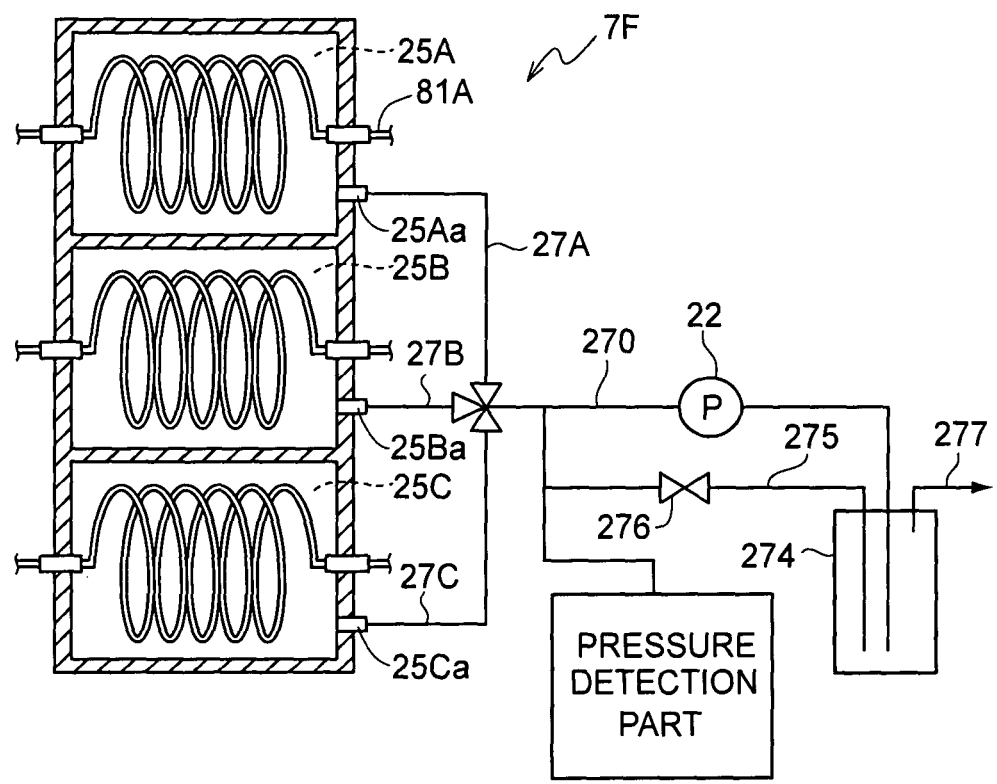
FIG. 9 is a sectional view corresponding to FIG. 2 for explaining a deaerator according to a seventh embodiment of the present invention.

In FIG. 9, a deaerator 7F according to a seventh embodiment of the present invention is illustrated. The deaerator 7F is configured so as to decrease the difference in the oxygen partial pressures of the reduced-pressure spaces 25A, 25B, and 25C between the initial stage of driving and after driving for a certain time, similarly to the deaerator 7E (see FIG. 8) according to the sixth embodiment of the present invention.

More specifically, the deaerator 7F is provided with: an exhaust sub-chamber 274 for holding a deacration gas from the exhaust outlets 25Aa, 25Ba, and 25Ca and the exhaust pipes 27A, 27B, 27C, and 270; a return pipe 275 for returning the deaeration gas of the exhaust sub-chamber 274 into the reduced-pressure spaces 25A, 25B, and 25C; a valve 276, which is provided at an intermediate portion of the return pipe 275; and an open-to-atmosphere pipe 277. The valve 276 is set in the closed state during deaeration, and is set in the open state after deaeration, by a control means (not shown in the drawing).

In the deaerator 7F, since the valve 276 is in the closed state during deaeration, the gas in the reduced-pressure spaces 25A, 25B, and 25C is introduced into the exhaust sub-chamber 274 via the exhaust pipes 27A, 27B, 27C, and 270, and the gas of the exhaust sub-chamber 274 is discharged to the atmosphere via the open-to-atmosphere pipe 277. The valve 276 is opened after completion of deaeration, as a result of which the deaeraion gas in the exhaust sub-chamber 274 is introduced into the reduced-pressure spaces 25A, 25B, and 25C via the return pipe 275. Here, the deaeration gas in the exhaust sub-chamber 274 has an oxygen concentration (oxygen partial pressure) similar to those of the reduced-pressure spaces 25A, 25B, and 25C. Therefore, by returning the deaeration gas in the exhaust sub-chamber 274 to the reduced-pressure spaces 25A, 25B, and 25C after completion of deaeration, the difference in oxygen partial pressures in the reduced-pressure spaces 25A, 25B, and 25C between the initial stage of driving and after driving for a certain time can be decreased.

In the deaerator 7F, the valve 276 may be opened intermittently during continuous driving of the deaerator 7F. In this case, the oxygen concentration (oxygen partial pressure) of the reduced-pressure spaces 25A, 25B, and 25C is monitored, and the valve 276 is closed when the oxygen concentration (the oxygen partial pressure) exceeds a predetermined threshold value or at fixed intervals.

In the deaerator 7F, an open-to-atmosphere valve may be provided at the open-to-atmosphere pipe 277, or an open-to-atmosphere valve may be provided at the open-to-atmosphere port of the exhaust sub-chamber 274 to which the open-to-atmosphere pipe 277 is connected. The control of the opening and closing of the open-to-atmosphere valve is, for example, linked to turning on and off of the pressure-reducing pump 22. Specifically, whereas the open-to-atmosphere valve is set in the opened state when the pressure-reducing pump 22 is driven, the open-to-atmosphere valve is set in the closed state when the pressure-reducing pump 22 is not driven. According to the configuration, no atmospheric air is introduced into the exhaust sub-chamber 274 when the pressure-reducing pump 22 is not driven, and the degree of pressure reduction of the reduced-pressure spaces 25A, 25B, and 25C is decreased only by the gas in the exhaust sub-chamber 274. Therefore, the differences in the oxygen partial pressures of the reduced-pressure spaces 25A, 25B, and 25C between the initial stage of driving of the deaerator 7F and after driving for a certain time can be further decreased. The effects similar to the effects achieved in the case in which the open-to-atmosphere valve is provided can be obtained also in a case in which the introduction of atmospheric air into the exhaust sub-chamber 274 when the pressure-reducing pump 22 is not driven is prohibited or restricted by using a device other than the open-to-atmosphere valve, such as a check valve, the high pressure drop part 23A, 23B, 23C, 23, 23A', 23B', or 23C' of the deaerator 2, 7A, 7B, or 7C (FIG. 2, and FIGS. 4 to 6) described above, or a modified example thereof.

Further, the deaerator 7F may be configured in such a manner that the return pipe 275 is omitted, and that the deaeration gas in the exhaust sub-chamber 274 is returned to the reduced-pressure spaces 25A, 25B, and 25C by using the exhaust pipes 27A, 27B, 27C, and 270.

Figure 10:
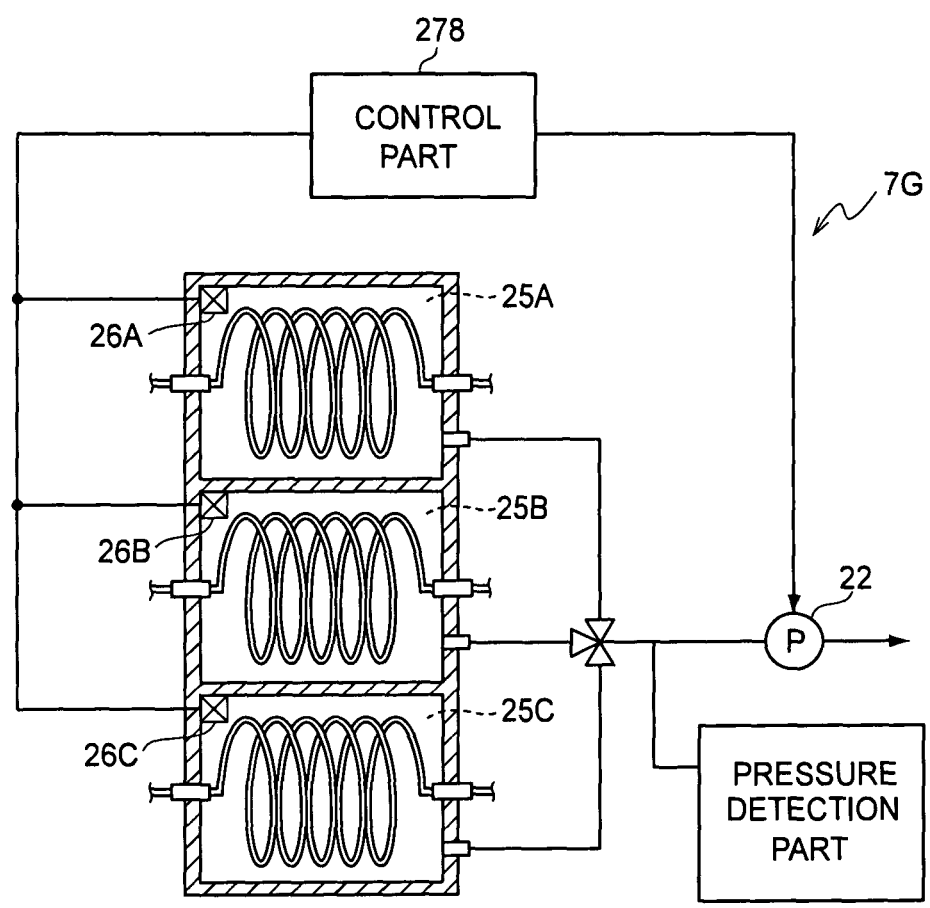
FIG. 10 is a sectional view corresponding to FIG. 2 for explaining a deaerator according to an eighth embodiment of the present invention.
Figure 12:
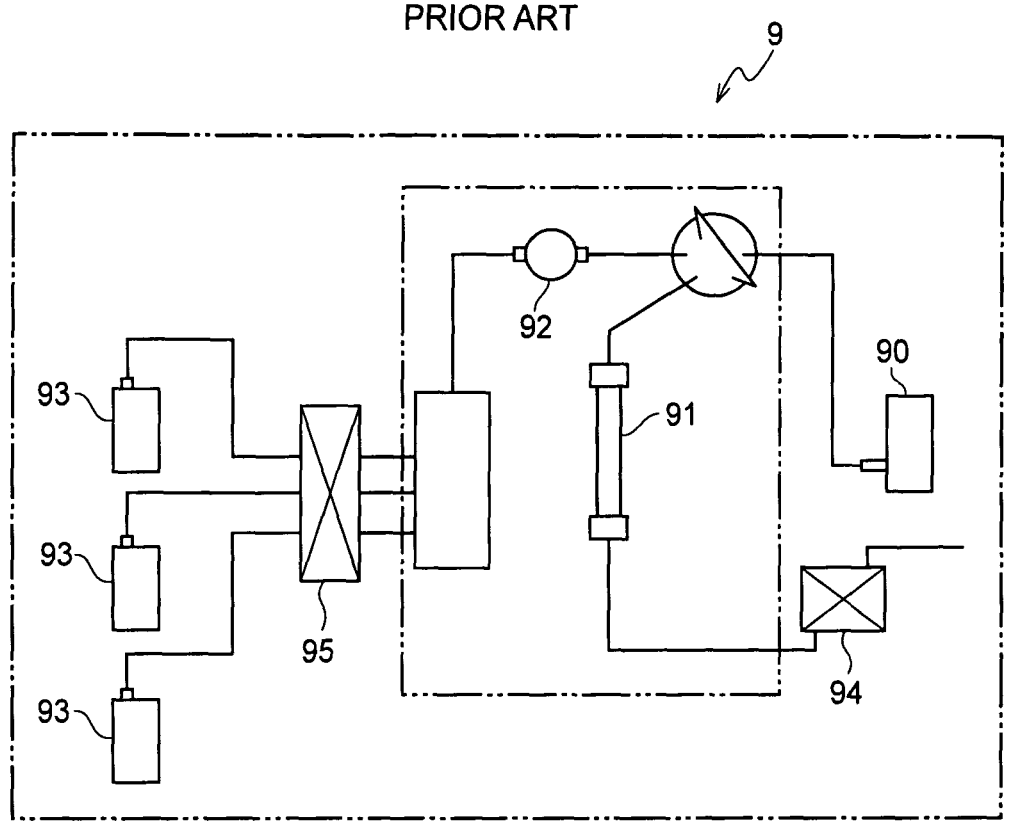
FIG. 12 is a schematic configuration diagram showing an example of a conventional HPLC apparatus (a high-performance liquid chromatograph).
Figure 13:
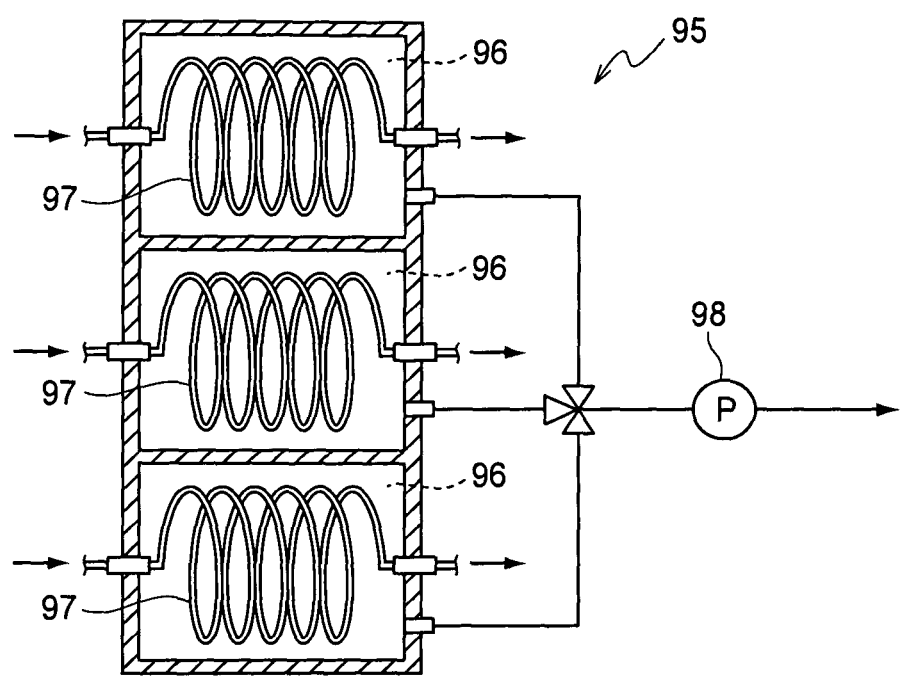
FIG. 13 is a sectional view schematically showing a part of the HPLC apparatus shown in FIG. 12 for explaining a deaerator.

In FIG. 10, a deaerator 7G according to an eighth embodiment of the present invention is illustrated. The deaerator 7G is configured so as to control the operation of the pressure-reducing pump 22 based on results of measurements of the oxygen concentrations (oxygen partial pressures) by the oxygen concentration measurement sensors 26A, 26B, and 26C, which are provided in the reduced-pressure spaces 25A, 25B, and 25C. More specifically, the deaerator 7G is configured so as to control the pressure-reducing pump 22 by a control part 278 when the oxygen concentration (the oxygen partial pressure) measured by the oxygen concentration measurement sensors 26A, 26B, and 26C has exceeded a fixed value, thereby increasing the degree of pressure reduction of the reduced-pressure spaces 25A, 25B, and 25C.

In such a deaerator 7G, even when the oxygen partial pressures of the reduced-pressure spaces 25A, 25B, and 25C increase, deaeration performance can be maintained constant by increasing the degree of pressure reduction in the reduced-pressure spaces 25A, 25B, and 25C.

The present invention is not limited to the embodiments described above, and various modifications thereto may be made. For example, application of the present invention is not limited to HPLC apparatuses for measuring a concentration of glycohemoglobin in blood, and the present invention can be applied to cases in which samples other than blood are used, cases in which components other than glycohemoglobin concentration are measured, and liquid chromatographs other than HPLC apparatuses.

Use of the deaerator according to the present invention is not limited to the liquid chromatograph, and the deaerator according to the present invention can be used also as a deaerator utilized for inhibition of oxidation or prevention of development of microorganisms in a manufacturing process of food, drinking water, or the like.

EXAMPLES

Hereinafter, a change in the glycohemoglobin concentration measurement value during continuous driving of the deaerator was studied.

Example 1

In the present example, measurements of the glycohemoglobin concentration in a whole blood were serially performed by using a glycohemoglobin measurement apparatus in which the deaerator 7E according to the sixth embodiment of the present invention is adopted (see FIG. 8). The glycohemoglobin measurement apparatus used was an apparatus obtained by improving the deaerator in "ADAMS A1c HA-8160" (manufactured by ARKRAY, Inc.) to the deaerator 7E having the configuration shown in FIG. 8. In the deaerator 7E, the valve 272 provided at an intermediate portion of the exhaust pipes 27A, 27B, 27C, and 270 was omitted. Before starting a measurement for the present Example, a fixed number of samples were continuously measured for glycohemoglobin by the improved glycohemoglobin measurement apparatus, and then the deaerator 7E was stopped. Then, external air was introduced from the exhaust pipes 27A, 27B, 27B, 27C, and 270 and the detection pipe 271 into the reduced-pressure spaces 25A, 25B, and 25B, thereby reducing the degree of pressure reduction of the reduced-pressure spaces 25A, 25B, and 25C. The time during which the deaerator 7E was not driven was set to about twelve hours. Whole blood collected from a patient of diabetes was used as the sample. Results of measurements of glycohemoglobin are shown in FIG. 11A.

Comparative Example 1

In the present Comparative Example, measurements of the glycohemoglobin concentration in the whole blood were serially performed in the same manner as in Example 1, except that the deaerator used in Comparative Example 1 was a deaerator in which the valve 272 was omitted and an open-to-atmosphere valve is provided in place of the airtight stopper 273 in the deaerator 7E. However, before measuring the concentration of glycohemoglobin in the present Comparative Example, the reduced-pressure spaces 25A, 25B, and 25C were left open to the atmosphere by opening the open-to-atmosphere valve; the open-to-atmosphere valve was in the closed state during measurements of the concentration of glycohemoglobin. Results of measurements of glycohemoglobin are shown in FIG. 11B.

As can be seen from FIGS. 11A and 11B, the measurement value decreased as the number of measured samples increased in Comparative Example 1; in contrast, in Example 1, although the initial measurement value was smaller than that of Comparative Example 1, the measurement value was approximately constant and stable even when the number of measured samples increased. From the results, it is understood that: in the case of opening the reduced-pressure space to the atmosphere after the deaerator is continuously driven, the measurement values vary if no measure is taken; in contrast, in a case in which variations in the oxygen concentrations (oxygen partial pressures) in the reduced-pressure spaces 25A, 25B, and 25C are suppressed so as to stabilize the degree of deaeration of the eluent in the deaerator and so as to equalize the concentrations of dissolved oxygen in the eluent, variations in measurement values are suppressed and the measurement accuracy can be improved even when the deaerator is continuously driven.

The invention claimed is:
1. A deaerator comprising:
   a liquid flow space;
   a reduced-pressure space;
   a gas permeable film that separates said spaces; and
   a pump for discharging a gas from within the reduced-pressure space to the outside,
   wherein the deaerator further comprises a gas partial pressure variation suppression means for suppressing variation in partial pressure of a specific gas in the reduced-pressure space, wherein
   the gas partial pressure variation suppression means is an oxygen partial pressure variation suppression means for suppressing variation in oxygen partial pressure in the reduced-pressure space, the oxygen partial pressure variation suppression means is configured so as to introduce a gas from the exterior of the deaerator into the reduced-pressure space during deaeration, the oxygen partial pressure variation suppression means has a high pressure drop part for increasing transfer resistance against the gas to be introduced into the reduced-pressure space, and the high pressure drop part comprises a porous filter.

2. The deaerator according to claim 1, wherein the oxygen partial pressure variation suppression means further has an external air inlet that allows the reduced-pressure space to communicate with the outside of the deaerator, and an external air introduction pipe connected to the external air inlet, and wherein the high pressure drop part is provided at an intermediate portion or end portion of the external air introduction pipe.

3. The deaerator according to claim 2, wherein the oxygen partial pressure variation suppression means has an oxygen partial pressure detection part for monitoring oxygen partial pressure of the reduced-pressure space, and a valve provided at an intermediate portion of the external air introduction pipe, and wherein the oxygen partial pressure variation suppression means is configured so as to control an open and closed state of the valve based on a result of monitoring by the oxygen partial pressure detection part.

4. The deaerator according to claim 1, further comprising:
an exhaust outlet that allows the reduced-pressure space to communicate with the outside of the deaerator; and
an exhaust pipe for discharging the gas in inside the reduced-pressure space via the exhaust outlet, a portion of the exhaust pipe extending between the exhaust outlet and the pump having high gas permeability,
wherein the oxygen partial pressure variation suppression means comprises the portion of the exhaust pipe having high gas permeability.

5. The deaerator according to claim 4, wherein the exhaust pipe is formed from the same material as that of the gas permeable film.

6. The deaerator according to claim 4, further comprising a branch pipe that is provided so as to branch from the exhaust pipe, wherein the branch pipe has high gas permeability and is closed at an intermediate portion thereof or at an end portion thereof.

7. The deaerator according to claim 4, wherein the oxygen partial pressure variation suppression means comprises a valve provided at an intermediate portion of the exhaust pipe, and the oxygen partial pressure variation suppression means is configured so as to set the valve in an open state during deaeration but to close the valve after completion of deaeration.

8. The deaerator according to claim 1, further comprising:
an exhaust outlet that allows the reduced-pressure space to communicate with the outside of the deaerator;
an exhaust sub-chamber for holding a gas drawn from the reduced-pressure space; and
an exhaust pipe for connecting the exhaust outlet and the exhaust sub-chamber,
wherein the oxygen partial pressure variation suppression means is configured so as to return the gas in the exhaust sub-chamber to the reduced-pressure space after completion of deaeration.

9. The deaerator according to claim 8, wherein the oxygen partial pressure variation suppression means has a return pipe for returning the gas in the exhaust sub-chamber to the reduced-pressure space, and a valve provided at an intermediate portion of the return pipe, and wherein the oxygen partial pressure variation suppression means is configured so as to set the valve in a closed state during deaeration, and so as to open the valve after completion of deaeration, thereby returning the gas in the exhaust sub-chamber to the reduced-pressure space.

10. The deaerator according to claim 1, wherein the oxygen partial pressure variation suppression means is configured so as to open the reduced-pressure space to the atmosphere when the pump is not driven, and so as to open the reduced-pressure space to the atmosphere during driving of the pump only in a case in which a fixed condition has been satisfied.

11. The deaerator according to claim 10, wherein the oxygen partial pressure variation suppression means is configured so as to open the reduced-pressure space to the atmosphere at fixed intervals or when a partial pressure of an oxygen gas in the reduced-pressure space becomes equal to or greater than a fixed value.

12. The deaerator according to claim 1, wherein the oxygen partial pressure variation suppression means is configured so as to increase a degree of pressure reduction of the reduced-pressure space when a partial pressure of an oxygen gas in the reduced-pressure space becomes equal to or greater than a fixed value.

13. A liquid chromatograph comprising:
a column that holds a packing material;
one or a plurality of eluent holding parts each holding an eluent to be supplied to the column; and
a deaerator for deaerating the eluent during supply of the eluent from an eluent holding part to the column;
wherein the deaerator includes:
a liquid flow space;
a reduced-pressure space;
a gas permeable film that separates said spaces;
a pump for discharging a gas from within the reduced-pressure space to the outside; and
a gas partial pressure variation suppression means for suppressing variation in partial pressure of a specific gas in the reduced-pressure space,
wherein the gas partial pressure variation suppression means is an oxygen partial pressure variation suppression means for suppressing variation in oxygen partial pressure in the reduced-pressure space,
wherein the oxygen partial pressure variation suppression means is configured so as to introduce a gas from the exterior of the deaerator into the reduced-pressure space during deaeration,
wherein the oxygen partial pressure variation suppression means has a high pressure drop part for increasing transfer resistance against the gas to be introduced into the reduced-pressure space, and
wherein the high pressure drop part comprises a porous filter.

14. The liquid chromatograph according to claim 13, wherein the oxygen partial pressure variation suppression means further has an external air inlet that allows the reduced-pressure space to communicate with the outside of the deaerator, and an external air introduction pipe connected to the external air inlet, and wherein the high pressure drop part is provided at an intermediate portion or end portion of the external air introduction pipe.

15. The liquid chromatograph according to claim 14, wherein the oxygen partial pressure variation suppression means has an oxygen partial pressure detection part for monitoring oxygen partial pressure of the reduced-pressure space, and a valve provided at an intermediate portion of the external air introduction pipe, and wherein the oxygen partial pressure variation suppression means is configured so as to control an open and closed state of the valve based on a result of monitoring by the oxygen partial pressure detection part.

16. The liquid chromatograph according to claim 13, further comprising:
   an exhaust outlet that allows the reduced-pressure space to communicate with the outside of the deaerator; and
   an exhaust pipe for discharging the gas inside the reduced-pressure space via the exhaust outlet, a portion of the exhaust pipe extending between the exhaust outlet and the pump having high gas permeability,
   wherein the oxygen partial pressure variation suppression means comprises the portion of the exhaust pipe having high gas permeability.

17. The liquid chromatograph according to claim 16, wherein the exhaust pipe is formed from the same material as that of the gas permeable film.

18. The liquid chromatograph according to claim 17, further comprising a branch pipe that is provided so as to branch from the exhaust pipe, wherein the branch pipe has high gas permeability and is closed at an intermediate portion thereof or at an end portion thereof.

19. The liquid chromatograph according to claim 17, wherein the oxygen partial pressure variation suppression means comprises a valve provided at an intermediate portion of the exhaust pipe, and the oxygen partial pressure variation suppression means is configured so as to set the valve in the open state during deaeration but to close the valve after completion of deaeration.

20. The liquid chromatograph according to claim 13, further comprising:
   an exhaust outlet that allows the reduced-pressure space to communicate with the outside of the deaerator;
   an exhaust sub-chamber for holding a gas drawn from the reduced-pressure space; and
   an exhaust pipe for connecting the exhaust outlet and the exhaust sub-chamber,
   wherein the oxygen partial pressure variation suppression means is configured so as to return the gas in the exhaust sub-chamber to the reduced-pressure space after completion of deaeration.

21. The liquid chromatograph according to claim 20, wherein the oxygen partial pressure variation suppression means has a return pipe for returning the gas in the exhaust sub-chamber to the reduced-pressure space, and a valve provided at an intermediate portion of the return pipe, and wherein the oxygen partial pressure variation suppression means is configured so as to set the valve in a closed state during deaeration, and so as to open the valve after completion of deaeration, thereby returning the gas in the exhaust sub-chamber to the reduced-pressure space.

22. The liquid chromatograph according to claim 13, wherein the oxygen partial pressure variation suppression means is configured so as to open the reduced-pressure space to the atmosphere when the pump is not driven, and so as to open the reduced-pressure space to the atmosphere during driving of the pump only in a case in which a fixed condition has been satisfied.

23. The liquid chromatograph according to claim 21, wherein the oxygen partial pressure variation suppression means is configured so as to open the reduced-pressure space to the atmosphere at fixed intervals or when the partial pressure of an oxygen gas in the reduced-pressure space becomes equal to or greater than a fixed value.

24. The liquid chromatograph according to claim 23, wherein the oxygen partial pressure variation suppression means is configured so as to increase a degree of pressure reduction of the reduced-pressure space when the partial pressure of an oxygen gas in the reduced-pressure space becomes equal to or greater than a predetermined value.

25. The liquid chromatograph according to claim 13, wherein the liquid chromatograph is configured so as to measure glycohemoglobin in a blood sample.

* * * * *